(12) United States Patent
Singh et al.

(10) Patent No.: US 9,085,504 B2
(45) Date of Patent: Jul. 21, 2015

(54) SOLVENT COMPOSITIONS CONTAINING FLUORINE SUBSTITUTED OLEFINS AND METHODS AND SYSTEMS USING SAME

(75) Inventors: Rajiv R. Singh, Getzville, NY (US); Raymond H. Thomas, Pendleton, NY (US); Gary Knopeck, Lakeview, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 11/850,018

(22) Filed: Sep. 4, 2007

(65) Prior Publication Data

US 2008/0171652 A1    Jul. 17, 2008

Related U.S. Application Data

(60) Division of application No. 11/475,605, filed on Jun. 26, 2006, and a continuation-in-part of application No. 10/837,525, filed on Apr. 29, 2004, now Pat. No. 7,279,451, which is a continuation-in-part of application No. 10/694,273, filed on Oct. 27, 2003, said application No. 10/837,525 is a continuation-in-part of application No. 10/694,272, filed on Oct. 27, 2003, now Pat. No. 7,230,146.

(60) Provisional application No. 60/693,853, filed on Jun. 24, 2005, provisional application No. 60/421,263, filed on Oct. 25, 2002, provisional application No. 60/421,435, filed on Oct. 25, 2002.

(51) Int. Cl.

| | | |
|---|---|---|
| C11D 17/00 | (2006.01) | |
| C07C 19/08 | (2006.01) | |
| C07C 19/10 | (2006.01) | |
| C07C 21/18 | (2006.01) | |
| C09K 3/30 | (2006.01) | |
| C09K 5/04 | (2006.01) | |

(52) U.S. Cl.
CPC ............... C07C 19/08 (2013.01); C07C 19/10 (2013.01); C07C 21/18 (2013.01); C09K 3/30 (2013.01); C09K 5/044 (2013.01); C09K 5/045 (2013.01); C09K 2205/106 (2013.01); C09K 2205/122 (2013.01); C09K 2205/126 (2013.01)

(58) Field of Classification Search
USPC ............. 252/68; 570/166, 153, 136; 510/412, 510/407, 408, 415, 410
See application file for complete search history.

(56) References Cited

U.S. PATENT DOCUMENTS

| | | | |
|---|---|---|---|
| 2,846,458 A | 8/1958 | Haluska | |
| 2,834,748 A | 10/1958 | Bailey et al. | |
| 2,889,379 A | 6/1959 | Ruh et al. | |
| 2,917,480 A | 12/1959 | Bailey et al. | |
| 2,931,840 A | 4/1960 | Marquis | |
| 2,996,555 A | 8/1961 | Rausch | |
| 3,085,918 A | 4/1963 | Sherliker et al. | |
| 3,723,318 A | 3/1973 | Butler | |
| 3,884,828 A | 5/1975 | Butler | |
| 4,465,786 A | 8/1984 | Zimmer et al. | |
| 4,788,352 A * | 11/1988 | Smutny ........................ 570/153 |
| 4,798,818 A | 1/1989 | Baizer et al. | |
| 4,944,890 A | 7/1990 | Deeb et al. | |
| 5,250,208 A | 10/1993 | Merchant et al. | |
| 5,532,419 A | 7/1996 | Van Der Puy et al. | |
| 5,578,137 A | 11/1996 | Shealy et al. | |
| 5,616,275 A | 4/1997 | Chisolm et al. | |
| 5,679,875 A | 10/1997 | Aoyamaeta et al. | |
| 5,714,083 A | 2/1998 | Turner | |
| 5,736,063 A | 4/1998 | Richard et al. | |
| 5,744,052 A | 4/1998 | Bivens | |
| 5,788,886 A | 8/1998 | Minor et al. | |
| 6,018,084 A * | 1/2000 | Nakada et al. ................ 570/166 |
| 6,041,621 A | 3/2000 | Oslzewski et al. | |
| 6,111,150 A * | 8/2000 | Sakyu et al. .................. 570/167 |
| 6,124,510 A | 9/2000 | Elsheikh et al. | |
| 6,258,292 B1 | 7/2001 | Turner | |
| 6,274,779 B1 | 8/2001 | Merkel et al. | |
| 6,300,378 B1 | 10/2001 | Tapscott | |
| 6,327,866 B1 | 12/2001 | Novak et al. | |
| 6,516,837 B2 | 2/2003 | Thomas et al. | |
| 6,688,118 B1 * | 2/2004 | Minor .............................. 62/114 |
| 6,858,571 B2 | 2/2005 | Pham et al. | |
| 6,972,271 B2 | 12/2005 | Thomas et al. | |
| 7,230,146 B2 | 6/2007 | Merkel et al. | |
| 7,248,809 B2 | 7/2007 | Kim et al. | |
| 7,279,451 B2 | 10/2007 | Singh et al. | |
| 2003/0127115 A1 | 7/2003 | Thomas et al. | |
| 2004/0089839 A1 | 5/2004 | Thomas et al. | |
| 2004/0119047 A1 | 6/2004 | Singh et al. | |
| 2005/0054741 A1 | 3/2005 | Zipfel et al. | |

FOREIGN PATENT DOCUMENTS

| | | |
|---|---|---|
| EP | 0398147 | 11/1990 |
| EP | 0644173 A1 | 5/1993 |
| EP | 0974571 | 1/2000 |
| EP | 1055439 | 11/2000 |
| EP | 1191080 | 7/2002 |
| GB | 950876 | 2/1964 |

(Continued)

OTHER PUBLICATIONS

Saunders and Frisch, "Polyurethanes Chemistry & Technology," vol. XVI, Part I and Part II Technology, John Wiley and Sons, New York, NY (1962), pp. 193-201 and 219-223.

Downing, Ralph C., "Fluorcarbon Refrigerants Handbook," Prentice Hall, Chapter 3 (1988), pp. 17-34.

*Primary Examiner* — Monique Peets

(74) *Attorney, Agent, or Firm* — Colleen D. Szuch

(57) ABSTRACT

Various compositions, including particularly solvent compositions, containing fluorinated olefins, including particularly tetra- and penta-fluoropropenes, in a variety of applications are disclosed.

10 Claims, 1 Drawing Sheet

(56) References Cited

FOREIGN PATENT DOCUMENTS

| JP | 2004110388 | 4/1992 |
| WO | 03/064508 | 8/2003 |
| WO | 2004/037752 | 5/2004 |
| WO | 2004/037913 | 5/2004 |
| WO | 2005/103187 | 11/2005 |
| WO | 2005/103188 | 11/2005 |
| WO | 2005/105947 | 11/2005 |

* cited by examiner

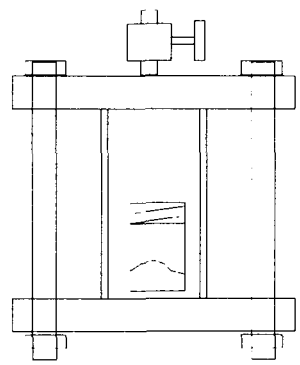

SOLVENT COMPOSITIONS CONTAINING FLUORINE SUBSTITUTED OLEFINS AND METHODS AND SYSTEMS USING SAME

RELATED APPLICATIONS

The present application is related to and claims the priority benefit of each of the following pending United States patent applications: U.S. application Ser. No. 11/475,605, filed Jun. 26, 2006 (now pending), which in turn is related to and claims the priority benefit of U.S. Provisional Application 60/693,853, filed Jun. 24, 2005; U.S. application Ser. No. 10/837,525, filed Apr. 29, 2004 (now pending), which in turn is a continuation in part of each of U.S. application Ser. No. 10/694,273 (now pending) and Ser. No. 10/694,272 (now U.S. Pat. No. 7,230,1463), each of which was filed Oct. 27, 2003, and each of which in turn is related to and claims the priority benefit of U.S. Provisional Applications 60/421,263 and 60/421,435, each of which was filed on Oct. 25, 2002. The disclosure of each of the patent applications and patents identified in the preceding sentence is incorporated herein by reference.

FIELD OF THE INVENTION

This invention relates to compositions, methods and systems having utility in numerous applications, including particularly heat transfer systems such as refrigeration systems. In preferred aspects, the present invention is directed to refrigerant compositions which comprise at least one multi-fluorinated olefin of the present invention.

BACKGROUND

Fluorocarbon based fluids have found widespread use in many commercial and industrial applications, including as the working fluid in systems such as air conditioning, heat pump and refrigeration systems, as aerosol propellants, as blowing agents, as heat transfer media, and as gaseous dielectrics. Because of certain suspected environmental problems, including the relatively high global warming potentials, associated with the use of some of the compositions that have heretofore been used in these applications, it has become increasingly desirable to use fluids having low or even zero ozone depletion potential, such as hydrofluorocarbons ("HFCs"). Thus, the use of fluids that do not contain chlorofluorocarbons ("CFCs") or hydrochlorofluorocarbons ("HCFCs") is desirable. Furthermore, some HFC fluids may have relatively high global warming potentials associated therewith, and it is desirable to use hydrofluorocarbon or other fluorinated fluids having as low global warming potentials as possible while maintaining the desired performance in use properties. Additionally, the use of single component fluids or azeotrope-like mixtures, which do not substantially fractionate on boiling and evaporation, is desirable in certain circumstances.

Certain fluorocarbons have been a preferred component in many heat exchange fluids, such as refrigerants, for many years in many applications. For, example, fluoroalkanes, such as chlorofluoromethane and chlorofluoroethane derivatives, have gained widespread use as refrigerants in applications including air conditioning and heat pump applications owing to their unique combination of chemical and physical properties. Many of the refrigerants commonly utilized in vapor compression systems are either single components fluids or azeotropic mixtures.

As suggested above, concern has been increasing in recent years about potential damage to the earth's atmosphere and climate, and certain chlorine-based compounds have been identified as particularly problematic in this regard. The use of chlorine-containing compositions (such as chlorofluorocarbons (CFC's), hydrochlorofluorocarbons (HCF's) and the like) as the working fluid in heat transfer systems, such as in refrigeration and air-conditioning systems, has become disfavored because of the ozone-depleting properties associated with many of such compounds. There has thus been an increasing need for new fluorocarbon and hydrofluorocarbon compounds and compositions that are attractive alternatives to the compositions heretofore used in these and other applications. For example, it has become desirable to retrofit chlorine-containing refrigeration systems by replacing chlorine-containing refrigerants with non-chlorine-containing refrigerant compounds that will not deplete the ozone layer, such as hydrofluorocarbons (HFC's). Industry in general and the heat transfer industry in particular are continually seeking new fluorocarbon based mixtures that offer alternatives to, and are considered environmentally safer substitutes for, CFCs and HCFCs. It is generally considered important, however, at least with respect to heat transfer fluids, that any potential substitute must also possess those properties present in many of the most widely used fluids, such as excellent heat transfer properties, chemical stability, low- or no-toxicity, non-flammability and/or lubricant compatibility, among others.

Applicants have come to appreciate that lubricant compatibility is of particular importance in many of applications. More particularly, it is highly desirably for refrigeration fluids to be compatible with the lubricant utilized in the compressor unit, used in most refrigeration systems. Unfortunately, many non-chlorine-containing refrigeration fluids, including HFC's, are relatively insoluble and/or immiscible in the types of lubricants used traditionally with CFC's and HFC's, including, for example, mineral oils, alkylbenzenes or poly (alpha-olefins). In order for a refrigeration fluid-lubricant combination to work at a desirable level of efficiently within a compression refrigeration, air-conditioning and/or heat pump system, the lubricant should be sufficiently soluble in the refrigeration liquid over a wide range of operating temperatures. Such solubility lowers the viscosity of the lubricant and allows it to flow more easily throughout the system. In the absence of such solubility, lubricants tend to become lodged in the coils of the evaporator of the refrigeration, air-conditioning or heat pump system, as well as other parts of the system, and thus reduce the system efficiency.

With regard to efficiency in use, it is important to note that a loss in refrigerant thermodynamic performance or energy efficiency may have secondary environmental impacts through increased fossil fuel usage arising from an increased demand for electrical energy.

Furthermore, it is generally considered desirably for CFC refrigerant substitutes to be effective without major engineering changes to conventional vapor compression technology currently used with CFC refrigerants.

Flammability is another important property for many applications. That is, it is considered either important or essential in many applications, including particularly in heat transfer applications, to use compositions which are non-flammable. Thus, it is frequently beneficial to use in such compositions compounds which are nonflammable. As used herein, the term "nonflammable" refers to compounds or compositions which are determined to be nonflammable as determined in accordance with ASTM standard E-681, dated 2002, which is incorporated herein by reference. Unfortunately, many HFC's which might otherwise be desirable for used in refrigerant compositions are not nonflammable. For example, the fluoroalkane difluoroethane (HFC-152a) and the fluoroalkene 1,1,1-trifluorpropene (HFO-1243zf) are each flammable and therefore not viable for use in many applications.

Higher fluoroalkenes, that is fluorine-substituted alkenes having at least five carbon atoms, have been suggested for use as refrigerants. U.S. Pat. No. 4,788,352—Smutny is directed to production of fluorinated $C_5$ to $C_8$ compounds having at least some degree of unsaturation. The Smutny patent identifies such higher olefins as being known to have utility as refrigerants, pesticides, dielectric fluids, heat transfer fluids, solvents, and intermediates in various chemical reactions. (See column 1, lines 11-22).

While the fluorinated olefins described in Smutny may have some level of effectiveness in heat transfer applications, it is believed that such compounds may also have certain disadvantages. For example, some of these compounds may tend to attack substrates, particularly general-purpose plastics such as acrylic resins and ABS resins. Furthermore, the higher olefinic compounds described in Smutny may also be undesirable in certain applications because of the potential level of toxicity of such compounds which may arise as a result of pesticide activity noted in Smutny. Also, such compounds may have a boiling point which is too high to make them useful as a refrigerant in certain applications.

Bromofluoromethane and bromochlorofluoromethane derivatives, particularly bromotrifluoromethane (Halon 1301) and bromochlorodifluoromethane (Halon 1211) have gained widespread use as fire extinguishing agents in enclosed areas such as airplane cabins and computer rooms. However, the use of various halons is being phased out due to their high ozone depletion. Moreover, as halons are frequently used in areas where humans are present, suitable replacements must also be safe to humans at concentrations necessary to suppress or extinguish fire.

Applicants have thus come to appreciate a need for compositions, and particularly heat transfer compositions, fire extinguishing/suppression compositions, blowing agents, solvent compositions, and compatabilizing agents, that are potentially useful in numerous applications, including vapor compression heating and cooling systems and methods, while avoiding one or more of the disadvantages noted above.

BRIEF DESCRIPTION OF THE DRAWINGS

FIG. 1 provides a sketch of the vessel as discussed in Example 5.

SUMMARY

Applicants have found that the above-noted need, and other needs, can be satisfied by compositions, preferably heat transfer compositions, comprising one or more C3 to C6 fluorakenes, and more preferably one or more C3, C4, or C5 fluoroalkenes, preferably compounds having Formula I as follows:

$$XCF_zR_{3-z} \quad (I)$$

where X is a $C_2$, $C_3$, $C_4$ or $C_5$ unsaturated, substituted or unsubstituted, radical, each R is independently Cl, F, Br, I or H, and z is 1 to 3. In certain preferred embodiments, the fluoroalkene of the present invention has at least four (4) halogen substituents, at least three of which are F and even more preferably none of which are Br. In certain preferred embodiments, the compound of formula one comprises a compound, and preferably a three carbon compound, in which each non-terminal unsaturated carbon has a fluorine substituent.

For embodiments in which at least one Br substituent is present, it is preferred that the compound includes no hydrogen. In such embodiments it also generally preferred that the Br substituent is on an unsaturated carbon, and even more preferably the Br substituent is on an non-terminal unsaturated carbon. One particularly preferred embodiment in this class is $CF_3CBr=CF_2$, including all of its isomers.

In certain embodiments it is highly preferred that the compounds of Formula I comprise propenes, butenes, pentanes and hexanes having from 3 to 5 fluorine substituents, with other substituents being either present or not present. In certain preferred embodiments, no R is Br, and preferably the unsaturated radical contains no Br substituents. Among the propenes, tetrafluoropropenes (HFO-1234) and fluorochloroporpenes (such as trifluoro,monochloropropenes (HFCO-1233), and even more preferably $CF_3CCl=CH_2$ (HFO-1233xf) and $CF_3CH=CHCl$ (HFO-1233zd)) are especially preferred in certain embodiments.

In certain embodiments, pentafluoropropenes are preferred, including particularly those pentafluoropropenes in which there is a hydrogen substituent on the terminal unsaturated carbon, such as $CF_3CF=CFH$ (HFO-1225yez and/or yz), particularly since applicants have discovered that such compounds have a relatively low degree of toxicity in comparison to at least the compound $CF_3CH=CF_2$ (HFO-1225zc).

Among the butenes, fluorochlorobutenes are especially preferred in certain embodiments.

The term "HFO-1234" is used herein to refer to all tetrafluoropropenes. Among the tetrafluoropropenes are included 1,1,1,2-tetrafluoropropene (HFO-1234yf) and both cis- and trans-1,1,1,3-tetrafluoropropene (HFO-1234ze). The term HFO-1234ze is used herein generically to refer to 1,1,1,3-tetrafluoropropene, independent of whether it is the cis- or trans-form. The terms "cis HFO-1234ze" and "transHFO-1234ze" are used herein to describe the cis- and trans-forms of 1,1,1,3-tetrafluoropropene respectively. The term "HFO-1234ze" therefore includes within its scope cis HFO-1234ze, transHFO-1234ze, and all combinations and mixtures of these.

The term "HFO-1233" is used herein to refer to all trifluoro,monochloropropenes. Among the trifluoro,monochloropropenes are included 1,1,1,trifluoro-2,chloro-propene (HFCO-1233xf), both cis- and trans-1,1,1-trifluo-3,chlororopropene (HFCO-1233zd). The term HFCO-1233zd is used herein generically to refer to 1,1,1-trifluo-3,chloropropene, independent of whether it is the cis- or trans-form. The terms "cis HFCO-1233zd" and "transHFCO-1233zd" are used herein to describe the cis- and trans-forms of 1,1,1-trifluo,3-chlororopropene, respectively. The term "HFCO-1233zd" therefore includes within its scope cis HFCO-1233zd, transHFCO-1233zd, and all combinations and mixtures of these.

The term "HFO-1225" is used herein to refer to all pentafluoropropenes. Among such molecules are included 1,1,1,2,3 pentafluoropropene (HFO-1225yez), both cis- and trans-forms thereof. The term HFO-1225yez is thus used herein generically to refer to 1,1,1,2,3 pentafluoropropene, independent of whether it is the cis- or trans-form. The term "HFO-1225yez" therefore includes within its scope cis HFO-1225yez, transHFO-1225yez, and all combinations and mixtures of these.

In certain preferred embodiments, the present compositions comprise a combination of two or more compounds of Formula I. In one such preferred embodiment the composition comprises at least one tetrafluoropropene and at least one pentafluoropropene compound, preferably with each compound being present in the composition in an amount of from about 20% by weight to about 80% by weight, more preferably from about 30% by weight to about 70% by weight, and even more preferably from about 40% by weight to about 60% by weight. In certain of such embodiments, the tetrafluoropropene comprises, and preferably consists essentially of HFO-1234 (most preferably HFO-1234yf) and HFO1225 (most preferably HFO-1225yez).

The present invention provides also methods and systems which utilize the compositions of the present invention, including methods and systems for heat transfer, for retrofitting existing heat transfer equipment, for replacing the existing heat transfer fluids in an existing heat transfer system. In certain cases, the present compositions may also be used in connection with foam blowing, solvating, flavor and fragrance extraction and/or delivery, aerosol generation, non-aerosol propellants and as inflating agents.

DETAILED DESCRIPTION OF PREFERRED EMBODIMENTS

The Compositions

The preferred embodiments of the present invention are directed to compositions comprising at least one fluoroalkene containing from 3 to 6 carbon atoms, preferably 3 to five carbon atoms, and in certain highly preferred embodiments three carbon atoms, and at least one carbon-carbon double bond. The fluoroalkene compounds of the present invention are sometimes referred to herein for the purpose of convenience as hydrofluoro-olefins or "HFOs" if they contain at least one hydrogen. Although it is contemplated that the HFOs of the present invention may contain two carbon-carbon double bonds, such compounds at the present time are not considered to be preferred. For HFOs which also contain at least one chlorine atom, the designation HFCO is sometimes used herein As mentioned above, the present compositions comprise one or more compounds in accordance with Formula I. In preferred embodiments, the compositions include compounds of Formula II below:

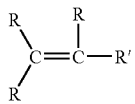

(II)

where each R is independently Cl, F, Br, I or H,

R' is $(CR_2)_n Y$,

Y is $CRF_2$ and n is 0, 1, 2 or 3, preferably 0 or 1, it being generally preferred however that when Br is present in the compound there is no hydrogen in the compound. In certain embodiments, Br is not present in the compound.

In highly preferred embodiments, Y is $CF_3$, n is 0 or 1 (most preferably 0) and at least one of the remaining Rs is F, and preferably no R is Br or when Br is present, there is no hydrogen in the compound.

Applicants believe that, in general, the compounds of the above identified Formulas I and II are generally effective and exhibit utility in heat transfer compositions generally and in refrigerant compositions particularly. The compositions of the present invention also find use as blowing agent compositions, compatibilzers, aerosols, propellants, fragrances, flavor formulations, solvent compositions and inflating agent composition. However, applicants have surprisingly and unexpectedly found that certain of the compounds having a structure in accordance with the formulas described above exhibit a highly desirable low level of toxicity compared to other of such compounds. As can be readily appreciated, this discovery is of potentially enormous advantage and benefit for the formulation of not only refrigerant compositions, but also any and all compositions which would otherwise contain relatively toxic compounds satisfying the formulas described above. More particularly, applicants believe that a relatively low toxicity level is associated with compounds of Formula II, preferably wherein Y is $CF_3$, n is 0 or 1, wherein at least one R on the unsaturated terminal carbon is H, and at least one of the remaining Rs is F or Cl. Applicants believe also that all structural, geometric and stereoisomers of such compounds are effective and of beneficially low toxicity.

In certain preferred embodiments the compounds of the present invention comprise one or more comprises a C3 or C4 HFO, preferably a C3 HFO, and preferably a compound accordance with Formula I in which X is a halogen substituted $C_3$ alkylene and z is 3. In certain of such embodiments X is fluorine and/or chlorine substituted $C_3$ alkylene, with the following $C_3$ alkylene radicals being preferred in certain embodiments:

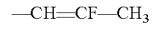

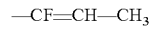

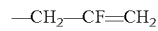

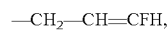

Such embodiments therefore comprise the following preferred compounds: $CF_3—CH=CF—CH_3$; $CF_3—CF=CH—CH_3$; $CF_3—CH_2—CF=CH_2$; $CF_3—CH_2—CH=CFH$; and combinations of these with one another and/or with other compounds in accordance with Formula I, In certain preferred embodiments, the compound of the present invention comprises a C3 or C4 HFCO, preferably a C3 HFCO, and more preferably a compound in accordance with Formula II in which Y is $CF_3$, n is 0, at least one R on the unsaturated terminal carbon is H, and at least one of the remaining Rs is Cl. HFCO-1233 is an example of such a preferred compound.

In highly preferred embodiments, especially embodiments which comprise the low toxicity compounds described above, n is zero. In certain highly preferred embodiments the compositions of the present invention comprise one or more tetrafluoropropenes, including HFO-1234yf, (cis)HFO-1234ze and (trans)HFO-1234ze, with HFO-1234ze being generally preferred. Although the properties of (cis)HFO-1234ze and (trans)HFO-1234ze differ in at least some respects, it is contemplated that each of these compounds is adaptable for use, either alone or together with other compounds including its stereo isomer, in connection with each of the applications, methods and systems described herein. For example, (trans) HFO-1234ze may be preferred for use in certain systems because of its relatively low boiling point (−19° C.), while (cis)HFO-1234ze, with a boiling point of +9° C., may be preferred in other applications. Of course, it is likely that combinations of the cis- and trans-isomers will be acceptable and/or preferred in many embodiments. Accordingly, it is to be understood that the terms "HFO-1234ze" and 1,3,3,3-tetrafluoropropene refer to both stereo isomers, and the use of this term is intended to indicate that each of the cis- and trans-forms applies and/or is useful for the stated purpose unless otherwise indicated.

HFO-1234 compounds are known materials and are listed in Chemical Abstracts databases. The production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786, each of which is incorporated herein by reference. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$. In addition, methods for producing compounds in accordance with the present invention are described generally in connection with pending United States patent application entitled "Process for Producing Fluorpropenes" bearing Ser. No. 10/694,272, which is also incorporated herein by reference.

Other preferred compounds for use in accordance with the present invention include pentafluoropropenes, including all isomers thereof (e.g., HFO-1225), tetra- and penta-fluorobutenes, including all isomers thereof (e.g., HFO-1354 and HFO-1345). Of course, the present compositions may comprise combinations of any two or more compounds within the broad scope of the invention or within any preferred scope of the invention.

The present compositions, particularly those comprising HFO-1234 (including HFO-1234ze and HFO-1234yf), are believed to possess properties that are advantageous for a number of important reasons. For example, applicants believe, based at least in part on mathematical modeling, that the fluoroolefins of the present invention will not have a substantial negative affect on atmospheric chemistry, being negligible contributors to ozone depletion in comparison to some other halogenated species. The preferred compositions of the present invention thus have the advantage of not contributing substantially to ozone depletion. The preferred compositions also do not contribute substantially to global warming compared to many of the hydrofluoroalkanes presently in use.

Of course other compounds and/or components that modulate a particular property of the compositions (such as cost for example) may also be included in the present compositions, and the presence of all such compounds and components is within the broad scope of the invention.

In certain preferred forms, compositions of the present invention have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100 year time horizon, as defined in "The Scientific Assessment of Ozone Depletion, 2002, a report of the World Meteorological Association's Global Ozone Research and Monitoring Project," which is incorporated herein by reference.

In certain preferred forms, the present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the Formula I compounds, particularly HFO-1234, and even more preferably HFO-1234yf, contained in the present compositions can vary widely, depending the particular application, and compositions containing more than trace amounts and less than 100% of the compound are within broad the scope of the present invention. Moreover, the compositions of the present invention can be azeotropic, azeotrope-like or non-azeotropic. In preferred embodiments, the present compositions comprise Formula I compounds, preferably HFO-1234 and more preferably HFO-1234ze and/or HFO-1234yf, preferably HFO-1234ze and/or HFO-1234yf, in amounts from about 5% by weight to about 99% by weight, and even more preferably from about 5% to about 95%. Many additional compounds or components, including lubricants, stabilizers, metal passivators, corrosion inhibitors, flammability suppressants, and other compounds and/or components that modulate a particular property of the compositions (such as cost for example) may be included in the present compositions, and the presence of all such compounds and components is within the broad scope of the invention. In certain preferred embodiments, the present compositions include, in addition to the compounds of formula I (including particularly HFO-1234ze and/or HFO-1234yf), one or more of the following:

Trichlorofluoromethane (CFC-11)
Dichlorodifluoromethane (CFC-12)
Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ The relative amount of any of the above noted compounds of the present invention, as well as any additional components which may be included in present compositions, can vary widely within the general broad scope of the present invention according to the particular application for the composition, and all such relative amounts are considered to be within the scope hereof.

Accordingly, applicants have recognized that certain compositions of the present invention can be used to great advantage in a number of applications. For example, included in the present invention are methods and compositions relating to heat transfer applications, foam and blowing agent applications, propellant applications, sprayable composition applications, sterilization applications, aerosol applications, compatibilizer application, fragrance and flavor applications, solvent applications, cleaning applications, inflating agent applications and others. It is believed that those of skill in the art will be readily able to adapt the present compositions for use in any and all such applications without undue experimentation.

The present compositions are generally useful as replacements for CFCs, such as dichlorodifluormethane (CFC-12), HCFCs, such as chlorodifluoromethane (HCFC-22), HFCs, such as tetrafluoroethane (HFC-134a), and combinations of HFCs and CFCs, such as the combination of CFC-12 and 1,1-difluorethane (HFC-152a) (the combination CFC-12:HFC-152a in a 73.8:26.2 mass ratio being known as R-500) in refrigerant, aerosol, and other applications.

Heat Transfer Compositions

The compositions of the present invention are generally adaptable for use in heat transfer applications, that is, as a heating and/or cooling medium, including as evaporative cooling agents.

In connection with evaporative cooling applications, the compositions of the present invention are brought in contact, either directly or indirectly, with a body to be cooled and thereafter permitted to evaporate or boil while in such contact, with the preferred result that the boiling gas in accordance with the present composition absorbs heat from the body to be cooled. In such applications it may be preferred to utilize the compositions of the present invention, preferably in liquid form, by spraying or otherwise applying the liquid to the body to be cooled. In other evaporative cooling applications, it may be preferred to permit a liquid composition in accordance with the present intention to escape from a relatively high pressure container into a relatively lower pressure environment wherein the body to be cooled is in contact, either directly or indirectly, with the container enclosing the liquid composition of the present invention, preferably without recovering or recompressing the escaped gas. One particular application for this type of embodiment is the self cooling of a beverage, food item, novelty item or the like. Previous to the invention described herein, prior compositions, such as HFC-152a and HFC-134a were used for such applications. However, such compositions have recently been looked upon negatively in such application because of the negative environmental impact caused by release of these materials into the atmosphere. For example, the United States EPA has determined that the use of such prior chemicals in this application is unacceptable due to the high global warming nature of these chemicals and the resulting detrimental effect on the environment that may result from their use. The compositions of the present invention should have a distinct advantage in this regard due to their low global warming potential and low ozone depletion potential, as described herein. Additionally, the present compositions are expected to also find substantial utility in connection with the cooling of electrical or electronic components, either during manufacture or during accelerated lifetime testing. In a accelerated lifetime testing, the component is sequentially heated and cooled in rapid succession to simulate the use of the component. Such uses would therefore be of particular advantage in the semiconductor and computer board manufacturing industry. Another advantage of the present compositions in this regard is they are expected to exhibit as contagious electrical properties when used in connection with such applications. Another evaporative cooling application comprises methods for temporarily causing a discontinuation of the flow of fluid through a conduit. Preferably, such methods would include contacting the conduit, such as a water pipe through which water is flowing, with a liquid composition according to the present invention and allowing the liquid composition of the present invention to evaporate while in contact with the conduit so as to freeze liquid contained therein and thereby temporarily stop the flow of fluid through the conduit. Such methods have distinct advantage in connection with enabling the service or other work to be performed on such conduits, or systems connected to such conduits, at a location downstream of the location at which the present composition is applied.

Although it is contemplated that the compositions of the present invention may include the compounds of the present invention in widely ranging amounts, it is generally preferred that refrigerant compositions of the present invention comprise compound(s) in accordance with Formula I, more preferably in accordance with Formula II, and even more preferably HFO-1234 (including HFO-1234ze and HFO-1234yf), in an amount that is at least about 50% by weight, and even more preferably at least about 70% by weight, of the composition. In certain embodiments, it is preferred that the heat transfer compositions of the present invention comprise tran- sHFO-1234ze. In certain preferred embodiments, it is preferred that the heat transfer compositions of the present invention comprise at least about 80%, and even more preferably at least about 90% by weight of HFO-1234, and even more preferably HFO-1234yf and/or HFO-1234ze. The heat transfer compositions of the present invention comprise in certain embodiments a combination of cis HFO-1234ze and transHFO1234ze, preferably in a cis:trans weight ratio of from about 1:99 to about 10:99, more preferably from about 1:99 to about 5:95, and even more preferably from about 1:99 to about 3:97.

The relative amount of the hydrofluoroolefin used in accordance with the present invention is preferably selected to produce a heat transfer fluid which has the required heat transfer capacity, particularly refrigeration capacity, and preferably is at the same time non-flammable. As used herein, the term non-flammable refers to a fluid which is non-flammable in all proportions in air as measured by ASTM E-681.

The compositions of the present invention may include other components for the purpose of enhancing or providing certain functionality to the composition, or in some cases to reduce the cost of the composition. For example, refrigerant compositions according to the present invention, especially those used in vapor compression systems, include a lubricant, generally in amounts of from about 30 to about 50 percent by weight of the composition. Furthermore, the present compositions may also include a co-refrigerant, or compatibilzer, such as propane, for the purpose of aiding compatibility and/or solubility of the lubricant. Such compatibilizers, including propane, butanes and pentanes, are preferably present in amounts of from about 0.5 to about 5 percent by weight of the composition. Combinations of surfactants and solubilizing agents may also be added to the present compositions to aid oil solubility, as disclosed by U.S. Pat. No. 6,516,837, the disclosure of which is incorporated by reference. Commonly used refrigeration lubricants such as Polyol Esters (POEs) and Poly Alkylene Glycols (PAGs), PAG oils, silicone oil, mineral oil, alkyl benzenes (ABs) and poly(alpha-olefin) (PAO) that are used in refrigeration machinery with hydrofluorocarbon (HFC) refrigerants may be used with the refrigerant compositions of the present invention. Commercially available mineral oils include Witco LP 250 (registered trademark) from Witco, Zerol 300 (registered trademark) from Shrieve Chemical, Sunisco 3GS from Witco, and Calumet RO15 from Calumet. Commercially available alkyl benzene lubricants include Zerol 150 (registered trademark). Commercially available esters include neopentyl glycol dipelargonate, which is available as Emery 2917 (registered trademark) and Hatcol 2370 (registered trademark). Other useful esters include phosphate esters, dibasic acid esters, and fluoroesters. In some cases, hydrocarbon based oils are have sufficient solubility with the refrigerant that is comprised of an iodocarbon, the combination of the iodocarbon and the hydrocarbon oil might more stable than other types of lubricant. Such combination may therefore be advantageous. Preferred lubricants include polyalkylene glycols and esters. Polyalkylene glycols are highly preferred in certain embodiments because they are currently in use in particular applications such as mobile air-conditioning. Of course, different mixtures of different types of lubricants may be used.

In certain preferred embodiments, the heat transfer composition comprises from about 10% to about 95% by weight of a compound of Formula I, more preferably a compound of Formula II, and even more preferably one or more HFO-1234 compounds, and from about 5% to about 90% by weight of an adjuvant, particular in certain embodiments a co-refrigerant (such as HFC-152, HFC-125 and/or $CF_3I$). The use of the term co-refrigerant is not intended for use herein in a limiting sense regarding the relative performance of the compound of Formula I compounds, but is used in stead used to identify other components of the refrigerant composition generally that contribute to the desirable heat transfer characteristics of the composition for a desired application. In certain of such embodiments the co-refrigerant comprises, and preferably consists essentially of, one or more HFCs and/or one or more fluoroiodo C1-3 compounds, such as trifluoroiodomethane, and combinations of these with each other and with other components.

In preferred embodiments in which the co-refrigerant comprises HFC, preferably HFC-125 the composition comprises HFC in an amount of from about 50% by weight to about 95% by weight of the total heat transfer composition, more preferably from about 60% by weight to about 90% by weight, and even more preferably of from about 70% to about 90% by weight of the composition. In such embodiments the compound of the present invention preferably comprises, and even more preferably consists essentially of, HFO-1234, and even more preferably HFO-1234yf and/or HFO-1234ze in an amount of from about 5% by weight to about 50% by weight of the total heat transfer composition, more preferably from about 10% by weight to about 40% by weight, and even more preferably of from about 10% to about 30% by weight of the composition.

In preferred embodiments in which the co-refrigerant comprises fluoriodocarbon, preferably $CF_3I$, the composition comprises fluoriodocarbon in an amount of from about 15% by weight to about 50% by weight of the total heat transfer composition, more preferably from about 20% by weight to about 40% by weight, and even more preferably of from about 25% to about 35% by weight of the composition. In such embodiments the compound of the present invention preferably comprises, and even more preferably consists essentially of, HFO-1234, and even more preferably HFO-1234yf in an amount of from about 50% by weight to about 90% by weight of the total heat transfer composition, more preferably from about 60% by weight to about 80% by weight, and even more preferably of from about 65% to about 75% by weight of the composition.

The present methods, systems and compositions are thus adaptable for use in connection with a wide variety of heat transfer systems in general and refrigeration systems in particular, such as air-conditioning (including both stationary and mobile air conditioning systems), refrigeration, heat-pump systems, and the like. In certain preferred embodiments, the compositions of the present invention are used in refrigeration systems originally designed for use with an HFC refrigerant, such as, for example, HFC-134a, or an HCFC refrigerant, such as, for example, HCFC-22. The preferred compositions of the present invention tend to exhibit many of the desirable characteristics of HFC-134a and other HFC refrigerants, including a GWP that is as low, or lower than that of conventional HFC refrigerants and a capacity that is as high or higher than such refrigerants and a capacity that is substantially similar to or substantially matches, and preferably is as high as or higher than such refrigerants. In particular, applicants have recognized that certain preferred embodiments of the present compositions tend to exhibit relatively low global warming potentials ("GWPs"), preferably less than about 1000, more preferably less than about 500, and even more preferably less than about 150. In addition, the relatively constant boiling nature of certain of the present compositions, including the azeotrope-like compositions described in the co-pending patent applications incorporated herein by reference, makes them even more desirable than certain conventional HFCs, such as R-404A or combinations of HFC-32, HFC-125 and HFC-134a (the combination HFC-32:HFC-125:HFC134a in approximate 23:25:52 weight ratio is referred to as R-407C), for use as refrigerants in many applications. Heat transfer compositions of the present invention are particularly preferred as replacements for HFC-134, HFC-152a, HFC-22, R-12 and R-500.

In certain other preferred embodiments, the present compositions are used in refrigeration systems originally designed for use with a CFC-refrigerant. Preferred refrigeration compositions of the present invention may be used in refrigeration systems containing a lubricant used conventionally with CFC-refrigerants, such as mineral oils, polyalkylbenzene, polyalkylene glycol oils, and the like, or may be used with other lubricants traditionally used with HFC refrigerants. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers (including chillers using centrifugal compressors), transport refrigeration systems, commercial refrigeration systems and the like.

Many existing refrigeration systems are currently adapted for use in connection with existing refrigerants, and the compositions of the present invention are believed to be adaptable for use in many of such systems, either with or without system modification. Many applications the compositions of the present invention may provide an advantage as a replacement in smaller systems currently based on certain refrigerants, for example those requiring a small refrigerating capacity and thereby dictating a need for relatively small compressor displacements. Furthermore, in embodiments where it is desired to use a lower capacity refrigerant composition of the present invention, for reasons of efficiency for example, to replace a refrigerant of higher capacity, such embodiments of the present compositions provide a potential advantage. Thus, it is preferred in certain embodiments to use compositions of the present invention, particularly compositions comprising a substantial proportion of, and in some embodiments consisting essentially of the present compositions, as a replacement for existing refrigerants, such as: HFC-134a; CFC-12; HCFC-22; HFC-152a; combinations of pentfluoroethane (HFC-125), trifluorethane (HFC-143a) and tetrafluoroethane (HFC-134a) (the combination HFC-125:HFC-143a:HFC134a in approximate 44:52:4 weight ratio is referred to as R-404A); combinations of HFC-32, HFC-125 and HFC-134a (the combination HFC-32:HFC-125:HFC134a in approximate 23:25:52 weight ratio is referred to as R-407C); combinations of methylene fluoride (HFC-32) and pentfluoroethane (HFC-125) (the combination HFC-32:HFC-125 in approximate 50:50 weight ratio is referred to as R-410A); the combination of CFC-12 and 1,1-difluorethane (HFC-152a) (the combination CFC-12:HFC-152a in a 73.8:26.2 weight ratio is referred to R-500); and combinations of HFC-125 and HFC-143a (the combination HFC-125:HFC143a in approximate 50:50 weight ratio is referred to as R-507A). In certain embodiments it may also be beneficial to use the present compositions in connection with the replacement of refrigerants formed from the combination HFC-32:HFC-125:HFC134a in approximate 20:40:40 weight ratio, which is referred to as R-407A, or in approximate 15:15:70 weight ratio, which is referred to as R-407D. The present compositions are also believed to be suitable as replacements for the above noted compositions in other applications, such as aerosols, blowing agents and the like, as explained elsewhere herein.

In certain applications, the refrigerants of the present invention potentially permit the beneficial use of larger displacement compressors, thereby resulting in better energy efficiency than other refrigerants, such as HFC-134a. Therefore the refrigerant compositions of the present invention provide the possibility of achieving a competitive advantage on an energy basis for refrigerant replacement applications, including automotive air conditioning systems and devices, commercial refrigeration systems and devices, chillers, residential refrigerator and freezers, general air conditioning systems, heat pumps and the like.

Many existing refrigeration systems are currently adapted for use in connection with existing refrigerants, and the compositions of the present invention are believed to be adaptable for use in many of such systems, either with or without system modification. In many applications the compositions of the present invention may provide an advantage as a replacement in systems which are currently based on refrigerants having a relatively high capacity. Furthermore, in embodiments where it is desired to use a lower capacity refrigerant composition of the present invention, for reasons of cost for example, to replace a refrigerant of higher capacity, such embodiments of the present compositions provide a potential advantage. Thus, It is preferred in certain embodiments to use compositions of the present invention, particularly compositions comprising a substantial proportion of, and in some embodiments consisting essentially of, HFO-1234 (preferably HFO-1234ze and/or HFO-1234yf) as a replacement for existing refrigerants, such as HFC-134a. In certain applications, the refrigerants of the present invention potentially permit the beneficial use of larger displacement compressors, thereby resulting in better energy efficiency than other refrigerants, such as HFC-134a. Therefore the refrigerant compositions of the present invention, particularly compositions comprising HFO-1234yf and/or HFO-1234ze (preferably transHFO-1234ze), provide the possibility of achieving a competitive advantage on an energy basis for refrigerant replacement applications.

It is contemplated that the compositions of the present, including particularly those which comprise HFO-1234yf and/or HFO-1234ze, also have advantage (either in original systems or when used as a replacement for refrigerants such as CFC-11, CFC-12, HCFC-22, HFC-134a, HFC-152a, R-500 and R-507A), in chillers typically used in connection with commercial air conditioning systems. In certain of such embodiments it is preferred to include in the present compositions, particularly those comprising HFO-1234yf and/or HFO-1234ze, from about 0.5 to about 30% of a supplemental flammability suppressant, and in certain cases more preferably 0.5% to about 15% by weight and even more preferably from about 0.5 to about 10% on a weight basis. In this regard it is noted that the certain of HFO-1234 and/or HFO-1225 components of the present compositions may in certain embodiments act as flammability suppressants with respect to other components in the composition. Thus, components other than HFO-1234 and HFO-1225 which have flammability suppressant functionality in the composition will sometimes be referred to herein as a supplemental flammability suppressant.

In certain preferred embodiments, the present compositions include, in addition to the compounds of formula I, particularly HFO-1234 (including HFO-1234ze and HFO-1234yf), one or more of the following additional compounds that may be included primarily for their impact on the heat transfer characteristics, cost and the like. The following components may thus be included in the compositions as co-heat transfer fluids (or co-refrigerants in the case of cooling operations):

Trichlorofluoromethane (CFC-11)
Dichlorodifluoromethane (CFC-12)
Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ Blowing Agents, Foams and Foamable Compositions Blowing agents may also comprise or constitute one or more of the present compositions. As mentioned above, the compositions of the present invention may include the compounds of the present invention in widely ranging amounts. It is generally preferred, however, that for preferred compositions for use as blowing agents in accordance with the present invention, compound(s) in accordance with Formula I, and even more preferably Formula II, are present in an amount that is at least about 5% by weight, and even more preferably at least about 15% by weight, of the composition. In certain preferred embodiments, the blowing agent comprises at least about 50% by weight of the present compositions, and in certain embodiments the blowing agent consists essentially of the present compositions. In certain preferred embodiments, the blowing agent compositions of the present invention and include, in addition to HFO-1234 (preferably HFO-1234ze and/or HFO-1234yf) one or more of co-blowing agents, fillers, vapor pressure modifiers, flame suppressants, stabilizers and like adjuvants. By way of example, one or more of the following components may included in certain preferred blowing agent of the present invention in widely varying amounts:

Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ It is contemplated that the blowing agent compositions of the present invention may comprise, preferably in amounts of at least about 15% by weight of the composition, HFO-1234yf, cis HFO-1234ze, transHFO1234ze or combinations of two or more of these. In certain preferred embodiments, the blowing agent compositions of the present invention comprise a combination of cis HFO-1234ze and transHFO1234ze in a cis: trans weight ratio of from about 1:99 to about 10:99, and even more preferably from about 1:99 to about 5:95.

In other embodiments, the invention provides foamable compositions. The foamable compositions of the present invention generally include one or more components capable of forming foam having a generally cellular structure and a blowing agent in accordance with the present invention. In certain embodiments, the one or more components comprise a thermosetting composition capable of forming foam and/or foamable compositions. Examples of thermosetting compositions include polyurethane and polyisocyanurate foam compositions, and also phenolic foam compositions. In such thermosetting foam embodiments, one or more of the present compositions are included as or part of a blowing agent in a foamable composition, or as a part of a two or more part foamable composition, which preferably includes one or more of the components capable of reacting and/or foaming under the proper conditions to form a foam or cellular structure. In certain other embodiments, the one or more components comprise thermoplastic materials, particularly thermoplastic polymers and/or resins. Examples of thermoplastic foam components include polyolefins, such as polystyrene (PS), polyethylene (PE), polypropylene (PP) and polyethyleneterepthalate (PET), and foams formed there from, preferably low-density foams. In certain embodiments, the thermoplastic foamable composition is an extrudable composition.

The invention also relates to foam, and preferably closed cell foam, prepared from a polymer foam formulation containing a blowing agent comprising the compositions of the invention. In yet other embodiments, the invention provides foamable compositions comprising thermoplastic or polyolefin foams, such as polystyrene (PS), polyethylene (PE), polypropylene (PP) and polyethyleneterpthalate (PET) foams, preferably low-density foams.

It will be appreciated by those skilled in the art, especially in view of the disclosure contained herein, that the order and manner in which the blowing agent of the present invention is formed and/or added to the foamable composition does not generally affect the operability of the present invention. For example, in the case of extrudable foams, it is possible that the various components of the blowing agent, and even the components of the present composition, be not be mixed in advance of introduction to the extrusion equipment, or even that the components are not added to the same location in the extrusion equipment. Thus, in certain embodiments it may be desired to introduce one or more components of the blowing agent at first location in the extruder, which is upstream of the place of addition of one or more other components of the blowing agent, with the expectation that the components will come together in the extruder and/or operate more effectively in this manner. Nevertheless, in certain embodiments, two or more components of the blowing agent are combined in advance and introduced together into the foamable composition, either directly or as part of premix which is then further added to other parts of the foamable composition.

In certain preferred embodiments, dispersing agents, cell stabilizers, surfactants and other additives may also be incorporated into the blowing agent compositions of the present invention. Surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is incorporated herein by reference. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl)phosphate, diammonium phosphate, various halogenated aromatic compounds, antimony oxide, aluminum trihydrate, polyvinyl chloride, and the like.

Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention.

Propellant and Aerosol Compositions

In another aspect, the present invention provides propellant compositions comprising or consisting essentially of a composition of the present invention. In certain preferred embodiments, such propellant composition is preferably a sprayable composition, either alone or in combination with other known propellants.

In one aspect, the present compositions may be used for propelling objects, including solid and/or liquid objects and/or gaseous objects, by applying to such objects a force generated by the present composition, such as would occur through the expansion of the compositions of the present invention. For example, such force may preferably be provided, at least in part, by the change of phase of the compositions of the present invention from liquid to gas, and/or by the force released as a result of a substantial pressure reduction as the composition of the present invention exits from a pressurized container. In this way, the compositions of the present invention may be used to apply a burst of force, or a sustained force to an object to be propelled. Accordingly, the present invention comprises systems, containers and devices which include compositions of the present invention and which are configured to propel or move an object, either a liquid object or a solid object or a gaseous object, with the desired amount of force. Examples of such uses include containers (such as pressurized cans and similar devices) which may be used, through the propellant force, to unblock drains, pipes or blockages in conduits, channels or nozzles. Another application includes use of the present composition to propel solid objects through the environment, particularly the ambient air, such as bullets, pellets, grenades, nets, canisters, bean bags, electrodes or other individual tethered or untethered projectiles. In other embodiments, the present compositions may be used to impart motion, such as a spitting motion, to gyroscopes, centrifuges, toys or other bodies to be rotated, or to impart a propelling force to solid objects, such as fireworks, confetti, pellets, munitions and other solid objects. In other applications, the force provided by the compositions of the present invention may be used to push or steer bodies in motion, including rockets or other projectiles.

The propellant compositions of the present invention preferably comprise a material to be sprayed and a propellant comprising, consisting essentially of, or consisting of a composition in accordance with the present invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleaning solvents, and lubricants, as well as medicinal materials such as anti-asthma medications. The term medicinal materials is used herein in its broadest sense to include any and all materials which are, or at least are believe to be, effective in connection with therapeutic treatments, diagnostic methods, pain relief, and similar treatments, and as such would include for example drugs and biologically active substances. The medicinal material in certain preferred embodiments are adapted to be inhaled. The medicament or other therapeutic agent is preferably present in the composition in a therapeutic amount, with a substantial portion of the balance of the composition comprising a compound of Formula I of the present invention, preferably HFO-1234, and even more preferably HFO-1234ze and/or HFO-1234yf.

Aerosol products for industrial, consumer or medical use typically contain one or more propellants along with one or more active ingredients, inert ingredients or solvents. The propellant provides the force that expels the product in aerosolized form. While some aerosol products are propelled with compressed gases like carbon dioxide, nitrogen, nitrous oxide and even air, most commercial aerosols use liquefied gas propellants. The most commonly used liquefied gas propellants are hydrocarbons such as butane, isobutane, and propane. Dimethyl ether and HFC-152a (1,1-difluoroethane) are also used, either alone or in blends with the hydrocarbon propellants. Unfortunately, all of these liquefied gas propellants are highly flammable and their incorporation into aerosol formulations will often result in flammable aerosol products.

Applicants have come to appreciate the continuing need for nonflammable, liquefied gas propellants with which to formulate aerosol products. The present invention provides compositions of the present invention, particularly and preferably compositions comprising HFO-1234, and even more preferably HFO-1234ze, for use in certain industrial aerosol products, including for example spray cleaners, lubricants, and the like, and in medicinal aerosols, including for example to deliver medications to the lungs or mucosal membranes. Examples of this includes metered dose inhalers (MDIs) for the treatment of asthma and other chronic obstructive pulmonary diseases and for delivery of medicaments to accessible mucous membranes or intranasally. The present invention thus includes methods for treating ailments, diseases and similar health related problems of an organism (such as a human or animal) comprising applying a composition of the present invention containing a medicament or other therapeutic component to the organism in need of treatment. In certain preferred embodiments, the step of applying the present composition comprises providing a MDI containing the composition of the present invention (for example, introducing the composition into the MDI) and then discharging the present composition from the MDI.

The compositions of the present invention, particularly compositions which comprise or consist essentially of HFO-1234ze, are capable of providing nonflammable, liquefied gas propellant and aerosols that do not contribute substantially to global warming. The present compositions can be used to formulate a variety of industrial aerosols or other sprayable compositions such as contact cleaners, dusters, lubricant sprays, and the like, and consumer aerosols such as personal care products, household products and automotive products. HFO-1234ze is particularly preferred for use as an important component of propellant compositions for in medicinal aerosols such as metered dose inhalers. The medicinal aerosol and/or propellant and/or sprayable compositions of the present invention in many applications include, in addition to compound of formula (I) or (II) (preferably HFO-1234ze), a medicament such as a beta-agonist, a corticosteroid or other medicament, and, optionally, other ingredients, such as surfactants, solvents, other propellants, flavorants and other excipients. The compositions of the present invention, unlike many compositions previously used in these applications, have good environmental properties and are not considered to be potential contributors to global warming. The present compositions therefore provide in certain preferred embodiments substantially nonflammable, liquefied gas propellants having very low Global Warming potentials.

Flavorants and Fragrances

The compositions of the present invention also provide advantage when used as part of, and in particular as a carrier for, flavor formulations and fragrance formulations. The suitability of the present compositions for this purpose is demonstrated by a test procedure in which 0.39 grams of Jasmone were put into a heavy walled glass tube. 1.73 grams of R-1234ze were added to the glass tube. The tube was then frozen and sealed. Upon thawing the tube, it was found that the mixture had one liquid phase. The solution contained 20 wt. % Jasome and 80 wt. % R-1234ze, thus establishing favorable use a carrier for flavor formulations and fragrances.

It also establishes its potential as an extractant of biologically active compounds (such as Biomass) and fragrances, including from plant matter. In certain embodiments, it may be preferred to use the present composition for in extraction applications with the present fluid in its supercritical state. This an other applications of involving use of the present compositions in the supercritical or near supercritical state are described hereinafter.

Inflating Agents

One potential advantage of the compositions of the present invention is that the preferred compositions are in a gaseous state under most ambient conditions. This characteristic allows them to fill the space while not adding significantly to the weight of the space being spilled. Furthermore, the compositions of the present invention are able to be compressed or liquefied for relatively easy transportation and storage. Thus, for example, the compositions of the present invention may be included, preferably but not necessarily in liquid form, in a closed container, such as a pressurized can, which has a nozzle therein adapted to release the composition into another environment in which it will exist, at least for a period of time, as a pressurized gas. For example, such an application may include including the present compositions in a can adapted to connect to tires such as may be used on transportation vehicles (including cars, trucks and aircraft). Other examples in accordance with this embodiment include the use of the present compositions, in a similar arrangement, to inflate air bags or other bladders (including other protective bladders) adapted to contain, at least for a period of time, a gaseous material under pressure. Alternatively to the use of a fixed container, such as I can, the present compositions may be applied in accordance with this aspect of the invention through a hose or other system that contains the present composition, either in liquid or gaseous form, and through which it can be introduced into such a pressurized environment as is required for the particular application.

Methods and Systems

The compositions of the present invention are useful in connection with numerous methods and systems, including as heat transfer fluids in methods and systems for transferring heat, such as refrigerants used in refrigeration, air conditioning and heat pump systems. The present compositions are also advantageous for in use in systems and methods of generating aerosols, preferably comprising or consisting of the aerosol propellant in such systems and methods. Methods of forming foams and methods of extinguishing and suppressing fire are also included in certain aspects of the present invention. The present invention also provides in certain aspects methods of removing residue from articles in which the present compositions are used as solvent compositions in such methods and systems.

Heat Transfer Methods and Systems

The preferred heat transfer methods generally comprise providing a composition of the present invention and causing heat to be transferred to or from the composition, either by sensible heat transfer, phase change heat transfer, or a combination of these. For example, in certain preferred embodiments the present methods provide refrigeration systems comprising a refrigerant of the present invention and methods of producing heating or cooling by condensing and/or evaporating a composition of the present invention. In certain preferred embodiments, the methods for cooling, including cooling of other fluid either directly or indirectly or a body directly or indirectly, comprise condensing a refrigerant composition comprising a composition of the present invention and thereafter evaporating said refrigerant composition in the vicinity of the article to be cooled. As used herein, the term "body" is intended to refer not only to inanimate objects but also to living tissue, including animal tissue in general and human tissue in particular. For example, certain aspects of the present invention involve application of the present composition to human tissue for one or more therapeutic purposes, such as a pain killing technique, as a preparatory anesthetic, or as part of a therapy involving reducing the temperature of the body being treated. In certain embodiments, the application to the body comprises providing the present compositions in liquid form under pressure, preferably in a pressurized container having a one-way discharge valve and/or nozzle, and releasing the liquid from the pressurized container by spraying or otherwise applying the composition to the body. As the liquid evaporates from the surface being sprayed, the surface cools.

Certain preferred methods for heating a fluid or body comprise condensing a refrigerant composition comprising a composition of the present invention in the vicinity of the fluid or body to be heated and thereafter evaporating said refrigerant composition. In light of the disclosure herein, those of skill in the art will be readily able to heat and cool articles according to the present inventions without undue experimentation.

Applicants have found that in the systems and methods of the present invention many of the important refrigeration system performance parameters are relatively close to the parameters for R-134a. Since many existing refrigeration systems have been designed for R-134a, or for other refrigerants with properties similar to R-134a, those skilled in the art will appreciate the substantial advantage of a low GWP and/or a low ozone depleting refrigerant that can be used as replacement for R-134a or like refrigerants with relatively minimal modifications to the system. It is contemplated that in certain embodiments the present invention provides retrofitting methods which comprise replacing the heat transfer fluid (such as a refrigerant) in an existing system with a composition of the present invention, without substantial modification of the system. In certain preferred embodiments the replacement step is a drop-in replacement in the sense that no substantial redesign of the system is required and no major item of equipment needs to be replaced in order to accommodate the composition of the present invention as the heat transfer fluid. In certain preferred embodiments, the methods comprise a drop-in replacement in which the capacity of the system is at least about 70%, preferably at least about 85%, and even more preferably at least about 90% of the system capacity prior to replacement. In certain preferred embodiments, the methods comprise a drop-in replacement in which the suction pressure and/or the discharge pressure of the system, and even more preferably both, is/are at least about 70%, more preferably at least about 90% and even more preferably at least about 95% of the suction pressure and/or the discharge pressure prior to replacement. In certain preferred embodiments, the methods comprise a drop-in replacement in which the mass flow of the system is at least about 80%, and even more preferably at least 90% of the mass flow prior to replacement.

In certain embodiments the present invention provides cooling by absorbing heat from a fluid or body, preferably by evaporating the present refrigerant composition in the vicinity of the body or fluid to be cooled to produce vapor comprising the present composition. Preferably the methods include the further step of compressing the refrigerant vapor, usually with a compressor or similar equipment to produce vapor of the present composition at a relatively elevated pressure. Generally, the step of compressing the vapor results in the addition of heat to the vapor, thus causing an increase in the temperature of the relatively high pressure vapor. Preferably in such embodiments the present methods include removing from this relatively high temperature, high pressure vapor at least a portion of the heat added by the evaporation and compression steps. The heat removal step preferably includes condensing the high temperature, high pressure vapor while the vapor is in a relatively high pressure condition to produce a relatively high pressure liquid comprising a composition of the present invention. This relatively high pressure liquid preferably then undergoes a nominally isoenthalpic reduction in pressure to produce a relatively low temperature, low pressure liquid. In such embodiments, it is this reduced temperature refrigerant liquid which is then vaporized by heat transferred from the body or fluid to be cooled.

In another process embodiment of the invention, the compositions of the invention may be used in a method for producing heating which comprises condensing a refrigerant comprising the compositions in the vicinity of a liquid or body to be heated. Such methods, as mentioned hereinbefore, frequently are reverse cycles to the refrigeration cycle described above.

Foam Blowing Methods

One embodiment of the present invention relates to methods of forming foams, and preferably polyurethane and polyisocyanurate foams. The methods generally comprise providing a blowing agent composition of the present inventions, adding (directly or indirectly) the blowing agent composition to a foamable composition, and reacting the foamable composition under the conditions effective to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above.

It is also possible to produce thermoplastic foams using the compositions of the invention. For example, conventional polystyrene and polyethylene formulations may be combined with the compositions in a conventional manner to produce rigid foams.

Cleaning Methods

The present invention also provides methods of removing containments from a product, part, component, substrate, or any other article or portion thereof by applying to the article a composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

Preferred methods of the present invention comprise applying the present composition to the article. Although it is contemplated that numerous and varied cleaning techniques can employ the compositions of the present invention to good advantage, it is considered to be particularly advantageous to use the present compositions in connection with supercritical cleaning techniques. Supercritical cleaning is disclosed in U.S. Pat. No. 6,589,355, which is assigned to the assignee of the present invention and incorporated herein by reference. For supercritical cleaning applications, is preferred in certain embodiments to include in the present cleaning compositions, in addition to the HFO-1234 (preferably HFO-1234ze), one or more additional components, such as $CO_2$ and other additional components known for use in connection with supercritical cleaning applications. It may also be possible and desirable in certain embodiments to use the present cleaning compositions in connection with particular vapor degreasing and solvent cleaning methods.

Flammability Reduction Methods

According to certain other preferred embodiments, the present invention provides methods for reducing the flammability of fluids, said methods comprising adding a compound or composition of the present invention to said fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the present compounds or compositions may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

Flame Suppression Methods

The present invention further provides methods of suppressing a flame, said methods comprising contacting a flame with a fluid comprising a compound or composition of the present invention. Any suitable methods for contacting the flame with the present composition may be used. For example, a composition of the present invention may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

Sterilization Methods

Many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with a compound or composition of the present invention comprising a compound of Formula I, preferably HFO-1234, and even more preferably HFO-1234ze, in combination with one or more sterilizing agents. While many sterilizing agents are known in the art and are considered to be adaptable for use in connection with the present invention, in certain preferred embodiments sterilizing agent comprises ethylene oxide, formaldehyde, hydrogen peroxide, chlorine dioxide, ozone and combinations of these. In certain embodiments, ethylene oxide is the preferred sterilizing agent. Those skilled in the art, in view of the teachings contained herein, will be able to readily determine the relative proportions of sterilizing agent and the present compound(s) to be used in connection with the present sterilizing compositions and methods, and all such ranges are within the broad scope hereof. As is known to those skilled in the art, certain sterilizing agents, such as ethylene oxide, are relatively flammable components, and the compound(s) in accordance with the present invention are included in the present compositions in amounts effective, together with other components present in the composition, to reduce the flammability of the sterilizing composition to acceptable levels.

The sterilization methods of the present invention may be either high or low-temperature sterilization of the present invention involves the use of a compound or composition of the present invention at a temperature of from about 250° F. to about 270° F., preferably in a substantially sealed chamber. The process can be completed usually in less than about 2 hours. However, some articles, such as plastic articles and electrical components, cannot withstand such high temperatures and require low-temperature sterilization. In low temperature sterilization methods, the article to be sterilized is exposed to a fluid comprising a composition of the present invention at a temperature of from about room temperature to about 200° F., more preferably at a temperature of from about room temperature to about 100° F.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

Supercritical Methods

It is contemplated that in general many of the uses and methods described herein can be carried out with the present compositions in the supercritical or near supercritical state. For example, the present compositions may be utilized in solvent and solvent extraction applications mentioned herein, particularly for use in connection with materials such as alkaloids (which are commonly derived from plant sources), for example caffeine, codeine and papaverine, for organometallic materials such as metallocenes, which are generally useful as catalysts, and for fragrances and flavors such as Jasmone.

The present compositions, preferably in their supercritical or near supercritical state, can be used in connection with methods involving the deposit of catalysts, particularly organometallic catalysts, on solid supports. In one preferred embodiment, these methods include the step of generating finely divided catalyst particles, preferably by precipitating such catalyst particles from the present compositions in the supercritical or near supercritical state. It is expected that in certain preferred embodiments catalysts prepared in accordance with the present methods will exhibit excellent activity.

It is also contemplated that certain of the MDI methods and devices described herein may utilize medicaments in finely divided form, and in such situations it is contemplated that the present invention provides methods which include the step of incorporating such finely divided medicament particles, such as albuterol, into the present fluids, preferably by dissolving such particles, in the present composition, preferably in the supercritical or near supercritical state. In cases where the solubility of the materials is relatively low when the present fluids are in the supercritical or near supercritical state, it may be preferred to use entrainers such as alcohols.

It is also contemplated that the present compositions in the supercritical or near supercritical state may be used to clean circuit boards and other electronic materials and articles.

Certain materials may have very limited solubility in the present compositions, particularly when in the supercritical or near supercritical state. For such situations, the present compositions may be used as anti-solvents for the precipitation of such low solubility solutes from solution in another supercritical or near supercritical solvent, such as carbon dioxide. For example, supercritical carbon dioxide is utilized frequently used in the extrusion process of thermoplastic foams, and the present compositions may be used to precipitation certain materials contained therein.

It is contemplated also that in certain embodiments it may be desirable to utilize the present compositions when in the supercritical or near supercritical state as a blowing agent.

EXAMPLES

The following examples are provided for the purpose of illustrating the present invention but without limiting the scope thereof.

Example 1

The coefficient of performance (COP) is a universally accepted measure of refrigerant performance, especially useful in representing the relative thermodynamic efficiency of a refrigerant in a specific heating or cooling cycle involving evaporation or condensation of the refrigerant. In refrigeration engineering, this term expresses the ratio of useful refrigeration to the energy applied by the compressor in compressing the vapor. The capacity of a refrigerant represents the amount of cooling or heating it provides and provides some measure of the capability of a compressor to pump quantities of heat for a given volumetric flow rate of refrigerant. In other words, given a specific compressor, a refrigerant with a higher capacity will deliver more cooling or heating power. One means for estimating COP of a refrigerant at specific operating conditions is from the thermodynamic properties of the refrigerant using standard refrigeration cycle analysis techniques (see for example, R. C. Downing, FLUOROCARBON REFRIGERANTS HANDBOOK, Chapter 3, Prentice-Hall, 1988).

A refrigeration/air conditioning cycle system is provided where the condenser temperature is about 150° F. and the evaporator temperature is about −35° F. under nominally isentropic compression with a compressor inlet temperature of about 50° F. COP is determined for several compositions of the present invention over a range of condenser and evaporator temperatures and reported in Table 1 below, based upon HFC-134a having a COP value of 1.00, a capacity value of 1.00 and a discharge temperature of 175° F.

TABLE 1

| REFRIGERANT COMPOSTION | Relative COP | Relative CAPACITY | DISCHARGE TEMPERATURE (° F.) |
|---|---|---|---|
| HFO 1225ye | 1.02 | 0.76 | 158 |
| HFO trans-1234ze | 1.04 | 0.70 | 165 |
| HFO cis-1234ze | 1.13 | 0.36 | 155 |
| HFO 1234yf | 0.98 | 1.10 | 168 |

This example shows that certain of the preferred compounds for use with the present compositions each have a better energy efficiency than HFC-134a (1.02, 1.04 and 1.13 compared to 1.00) and the compressor using the present refrigerant compositions will produce discharge temperatures (158, 165 and 155 compared to 175), which is advantageous since such result will likely leading to reduced maintenance problems. Moreover, it is evident from the above table that one embodiment of the present invention, namely one in which the refrigerant composition comprises, and preferably comprises at least about 70% by weight of HFO-1234yf, has a dramatically superior performance in terms of relative capacity in comparison not only to R-134a, but also to embodiments in which the refrigerant consists essentially of HFO-1234ze. In certain preferred embodiments, therefore the present invention provides methods for heating or cooling an article or fluid comprising using a composition comprising at least about 80% by weight of HFO-1234yf, and even more preferably at least about 90% by weight, and in which the capacity of the refrigeration system is at least about 100%, more preferably at least about 105%, of the capacity of the same system with R-134a used as the refrigerant.

Example 2

The miscibility of HFO-1225ye and HFO-1234ze with various refrigeration lubricants is tested. The lubricants tested are mineral oil (C3), alkyl benzene (Zerol 150), ester oil (Mobil EAL 22 cc and Solest 120), polyalkylene glycol (PAG) oil (Goodwrench Refrigeration Oil for 134a systems), and a poly(alpha-olefin) oil (CP-6005-100). For each refrigerant/oil combination, three compositions are tested, namely 5, 20 and 50 weight percent of lubricant, with the balance of each being the compound of the present invention being tested The lubricant compositions are placed in heavy-walled glass tubes. The tubes are evacuated, the refrigerant compound in accordance with the present invention is added, and the tubes are then sealed. The tubes are then put into an air bath environmental chamber, the temperature of which is varied from about −50° C. to 70° C. At roughly 10° C. intervals, visual observations of the tube contents are made for the existence of one or more liquid phases. In a case where more than one liquid phase is observed, the mixture is reported to be immiscible. In a case where there is only one liquid phase observed, the mixture is reported to be miscible. In those cases where two liquid phases were observed, but with one of the liquid phases occupying only a very small volume, the mixture is reported to be partially miscible.

The polyalkylene glycol and ester oil lubricants were judged to be miscible in all tested proportions over the entire temperature range, except that for the HFO-1225ye mixtures with polyalkylene glycol, the refrigerant mixture was found to be immiscible over the temperature range of −50° C. to −30° C. and to be partially miscible over from −20 to 50° C. At 50 weight percent concentration of the PAG in refrigerant and at 600, the refrigerant/PAG mixture was miscible. At 70° C., it was miscible from 5 weight percent lubricant in refrigerant to 50 weight percent lubricants in refrigerant.

Example 3

The compatibility of the refrigerant compounds and compositions of the present invention with PAG lubricating oils while in contact with metals used in refrigeration and air conditioning systems is tested at 350° C., representing conditions much more severe than are found in many refrigeration and air conditioning applications.

Aluminum, copper and steel coupons are added to heavy walled glass tubes. Two grams of oil are added to the tubes. The tubes are then evacuated and one gram of refrigerant is added. The tubes are put into an oven at 350° F. for one week and visual observations are made. At the end of the exposure period, the tubes are removed.

This procedure was done for the following combinations of oil and the compound of the present invention:
a) HFC-1234ze and GM Goodwrench PAG oil
b) HFC1243 zf and GM Goodwrench oil PAG oil
c) HFC-1234ze and MOPAR-56 PAG oil
d) HFC-1243 zf and MOPAR-56 PAG oil
e) HFC-1225 ye and MOPAR-56 PAG oil.

In all cases, there is minimal change in the appearance of the contents of the tube. This indicates that the refrigerant compounds and compositions of the present invention are stable in contact with aluminum, steel and copper found in refrigeration and air conditioning systems, and the types of lubricating oils that are likely to be included in such compositions or used with such compositions in these types of systems.

Comparative Example

Aluminum, copper and steel coupons are added to a heavy walled glass tube with mineral oil and CFC-12 and heated for one week at 350° C., as in Example 3. At the end of the exposure period, the tube is removed and visual observations are made. The liquid contents are observed to turn black, indicating there is severe decomposition of the contents of the tube.

CFC-12 and mineral oil have heretofore been the combination of choice in many refrigerant systems and methods. Thus, the refrigerant compounds and compositions of the present invention possess significantly better stability with many commonly used lubricating oils than the widely-used prior art refrigerant-lubricating oil combination.

Example 4

Polyol Foam

This example illustrates the use of blowing agent in accordance with one of the preferred embodiments of the present invention, namely the use of HFO-1234ze, and the production of polyol foams in accordance with the present invention. The components of a polyol foam formulation are prepared in accordance with the following Table 2:

TABLE 2

| | PBW |
|---|---|
| Polyol Component | |
| Voranol 490 | 50 |
| Voranol 391 | 50 |
| Water | 0.5 |
| B-8462 (surfactant) | 2.0 |
| Polycat 8 | 0.3 |
| Polycat 41 | 3.0 |
| HFO-1234ze | 35 |
| Total | 140.8 |
| Isocyanate | |
| M-20S | 123.8 Index 1.10 |

*Voranol 490 is a sucrose-based polyol and Voranol 391 is a toluene diamine based polyol, and each are from Dow Chemical. B-8462 is a surfactant available from Degussa-Goldschmidt. Polycat catalysts are tertiary amine based and are available from Air Products. Isocyanate M-20S is a product of Bayer LLC.

The foam is prepared by first mixing the ingredients thereof, but without the addition of blowing agent. Two Fisher-Porter tubes are each filled with about 52.6 grams of the polyol mixture (without blowing agent) and sealed and placed in a refrigerator to cool and form a slight vacuum. Using gas burets, about 17.4 grams of HFO-1234ze are added to each tube, and the tubes are then placed in an ultrasound bath in warm water and allowed to sit for 30 minutes. The solution produced is hazy, and a vapor pressure measurement at room temperature indicates a vapor pressure of about 70 psig indicating that the blowing agent is not in solution. The tubes are then placed in a freezer at 27° F. for 2 hours. The vapor pressure was again measured and found to be 14-psig. The isocyanate mixture, about 87.9 grams, is placed into a metal container and placed in a refrigerator and allowed to cool to about 50° F. The polyol tubes were then opened and weighed into a metal mixing container (about 100 grams of polyol blend are used). The isocyanate from the cooled metal container is then immediately poured into the polyol and mixed with an air mixer with double propellers at 3000 RPM's for 10 seconds. The blend immediately begins to froth with the agitation and is then poured into an 8×8×4 inch box and allowed to foam. Because of the froth, a cream time can not be measured. The foam has a 4-minute gel time and a 5-minute tack free time. The foam is then allowed to cure for two days at room temperature.

The foam is then cut to samples suitable for measuring physical properties and is found to have a density of 2.14 pcf. K-factors are measured and found to be as indicated in the following Table 3:

TABLE 3

| Temperature | K, BTU In/Ft² h ° F. |
|---|---|
| 40° F. | 0.1464 |
| 75° F. | 0.1640 |
| 110° F. | 0.1808 |

Example 5

Polystyrene Foam

This example illustrates the use of blowing agent in accordance with two preferred embodiments of the present invention, namely the use of HFO-1234ze and HFO-1234yf, and the production of polystyrene foam. A testing apparatus and protocol has been established as an aid to determining whether a specific blowing agent and polymer are capable of producing a foam and the quality of the foam. Ground polymer (Dow Polystyrene 685D) and blowing agent consisting essentially of HFO-1234ze are combined in a vessel. The vessel volume is 200 cm³ and it is made from two pipe flanges and a section of 2-inch diameter schedule 40 stainless steel pipe 4 inches long. The vessel is placed in an oven, with temperature set at from about 190° F. to about 285° F., preferably for polystyrene at 265° F., and remains there until temperature equilibrium is reached.

The pressure in the vessel is then released, quickly producing a foamed polymer. The blowing agent plasticizes the polymer as it dissolves into it. The resulting density of the two foams thus produced using this method are given in Table 4 and graphed in FIG. 1 as the density of the foams produced using trans-HFO-1234ze and HCO-1234yf. The data show that foam polystyrene is obtainable in accordance with the present invention. The die temperature for R1234ze with polystyrene is about 250° F. is determined and found to be acceptable.

TABLE 4

| | Dow polystyrene 685D Foam density (lb/ft³) | |
|---|---|---|
| T ° F. | transHFO-1234ze | HFO-1234yf |
| 275 | 55.15 | |
| 260 | 22.14 | 14.27 |
| 250 | 7.28 | 24.17 |
| 240 | 16.93 | |

Example 6

This example illustrates the performance of one embodiment of the present invention in which a refrigerant composition comprises HFO-1234 wherein a large proportion, and preferably at least about 75% by weight and even more preferably at least about 90% by weight, of the HFO-1234 is HFO-1234yf. More particularly, such a composition is used as a replacement for HFC-134a in four refrigerant systems. The first system is one have an evaporator temperature (ET) of about 20° F. and condenser temperature (CT) of about 130° F. (Example 6A). For the purposes of convenience, such heat transfer systems, that is, systems having an ET of from about 0 to about 35 and a CT of from about 80° F. to about 130° F., are referred to herein as "medium temperature" systems. The second system is one have an ET of about −10° F. and a CT of about 110° F. (Example 6B). For the purposes of convenience, such heat transfer systems, that is, systems having an evaporator temperature of from about −20° F. to about 20° F. and a CT of from about 80° F. to about 130° F., are referred to herein as "refrig/freezer" systems. The third system is one have an ET of about of 35° F. and a CT of about 150° F. (Example 6C). For the purposes of convenience, such heat transfer systems, that is, systems having an evaporator temperature of from about 30° F. to about 60° F. and a CT of from about 90° F. to about 200° F., are referred to herein as "automotive AC" systems. The fourth system is one have an ET of about 40° F. and a CT of about 60° F. (Example 6D). For the purposes of convenience, such heat transfer systems, that is, systems having an evaporator temperature of from about 35° F. to about 50° F. and a CT of from about 80° F. to about 120° F., are referred to herein as "chiller" or "chiller AC" systems The operation of each of such systems using R-134a and a refrigeration composition comprising at least about 90% by weight of HFO-1234yf is reported in Tables 6A-D below:

TABLE 6A

| Medium Temp Conditions 20° F. ET and 130° F. CT | | | |
|---|---|---|---|
| Performance Property | Units | R-134a | HFO-1234yf |
| Capacity* | Btu/hr | 2541 | 2519 |
| Rel to R-134a | % | | 99.1% |
| COP | — | 2.31 | 2.27 |
| Rel to R-134a | % | | 98.3% |
| Discharge Press. | psig | 198.7 | 190.3 |
| Rel to R-134a | % | | 95.8% |
| Suction Press. | psig | 18.4 | 22.5 |
| Rel to R-134a | % | | 122.3% |
| Mass Flow | lb/hr | 0.673 | 0.958 |
| Rel to R-134a | % | | 142.3% |

*Capacity per CFM of compressor displacement (Volumetric Capacity)

TABLE 6B

| Refrig/Freezer Temp Conditions 10° F. ET and 110° F. CT | | | |
|---|---|---|---|
| Performance Property | Units | R-134a | HFO-1234yf |
| Capacity* | Btu/hr | 1234 | 1293 |
| Rel to R-134a | % | | 104.8% |
| COP | — | 1.77 | 1.71 |
| Rel to R-134a | % | | 96.6% |
| Discharge Press. | psig | 146.4 | 145.4 |
| Rel to R-134a | % | | 99.3% |
| Suction Press. | psig | 1.9 | 6.0 |
| Rel to R-134a | % | | 315.8% |
| Mass Flow | lb/hr | 0.342 | 0.427 |
| Rel to R-134a | % | | 124.9% |

*Capacity per CFM of compressor displacement (Volumetric Capacity)

TABLE 6C

Auto AC Temp Conditions 35° F. ET and 150° F. CT

| Performance Property | Units | R-134a | HFO-1234yf |
|---|---|---|---|
| Capacity* | Btu/hr | 2754 | 2612 |
| Rel to R-134a | % | — | 94.8% |
| COP | — | 1.91 | 1.84 |
| Rel to R-134a | % | — | 96.3% |
| Discharge Press. | psig | 262.9 | 247.3 |
| Rel to R-134a | % | — | 94.1% |
| Suction Press. | psig | 30.4 | 34.5 |
| Rel to R-134a | % | — | 113.5% |
| Mass Flow | lb/hr | 0.891 | 1.235 |
| Rel to R-134a | % | — | 138.6% |

*Capacity per CFM of compressor displacement (Volumetric Capacity)

TABLE 6D

Chiller Temp Conditions 40° F. ET and 95° F. CT

| Performance Property | Units | R-134a | HFO-1234yf |
|---|---|---|---|
| Capacity* | Btu/hr | 4236 | 4060 |
| Rel to R-134a | % | — | 95.8% |
| COP | — | 6.34 | 6.23 |
| Rel to R-134a | % | — | 98.3% |
| Discharge Press. | psig | 113.9 | 113.5 |
| Rel to R-134a | % | — | 99.6% |
| Suction Press. | psig | 35.0 | 38.7 |
| Rel to R-134a | % | — | 110.6% |
| Mass Flow | lb/hr | 1.034 | 1.268 |
| Rel to R-134a | % | — | 122.6% |

*Capacity per CFM of compressor displacement (Volumetric Capacity)

As can be seen from the Tables above, many of the important refrigeration system performance parameters are relatively close to the parameters for R-134a. Since many existing refrigeration systems have been designed for R-134a, or for other refrigerants with properties similar to R-134a, those skilled in the art will appreciate the substantial advantage of a low GWP and/or a low ozone depleting refrigerant that can be used as replacement for R-134a or like refrigerants with relatively minimal modifications to the system. It is contemplated that in certain embodiments the present invention provided retrofitting methods which comprise replacing the refrigerant in an existing system with a composition of the present invention, preferably a composition comprising at least about 90% by weight and/or consists essentially of HFO-1234 and even more preferably HFO-1234yf, without substantial modification of the system. In certain preferred embodiments the replacement step is a drop-in replacement in the sense that no substantial redesign of the system is required and no major item of equipment needs to be replaced in order to accommodate the refrigerant of the present invention.

What is claimed is:

1. A method of solvating a contaminant material on a product, part, component, substrate, or other article or portion thereof, said method comprising:
   a. providing a solvent composition for solvating the contaminant material, said solvent composition comprising at least about 5% by weight of $CF_3CH=CHCl$ (HFCO-1233zd); and
   b. removing at least a portion of the contaminant material from the product, part, component, substrate, or other article or portion by solvating the contaminant material by contacting the product, part, component, substrate, or other article or portion with said solvating composition.

2. The method of claim 1 wherein said $CF_3CH=CHCl$ (HFCO-1233zd) comprises trans$CF_3CH=CHCl$ (transHFCO-1233zd).

3. The method of claim 1 wherein said $CF_3CH=CHCl$ (HFCO-1233zd) comprises cis$CF_3CH=CHCl$ (cisHFCO-1233zd).

4. The method of claim 1 wherein said solvent composition further comprises at least one additional component selected from the group consisting of from lubricants, stabilizers, metal passivators, corrosion inhibitors, flammability suppressants, trichlorofluoromethane (CFC-11), dichlorodifluoromethane (CFC-12), difluoromethane (HFC-32), pentafluoroethane (HFC-125), 1,1,2,2-tetrafluoroethane (HFC-134), 1,1,1,2-tetrafluoroethane (HFC-134a), difluoroethane (HFC-152a), 1,1,1,2,3,3,3-heptafluoropropane (HFC-227ea), 1,1,1,3,3,3-hexafluoropropane (HFC-236fa),1,1,1,3,3-pentafluoropropane (HFC-245fa), 1,1,1,3,3-pentafluorobutane (HFC-365mfc), water, $CO_2$, and combinations of two or more of these.

5. The method of claim 1 wherein said composition further comprises 1,1,1,3,3-pentafluorobutane (HFC-365mfc).

6. The method of claim 1 wherein said composition further comprises HFO-1234ze.

7. The method claim 1 wherein said product, part, component, substrate, or other article or portion thereof comprises a semiconductor.

8. The method of claim 1 wherein the solvent composition further comprises $CO_2$.

9. The method of claim 1 wherein the solvent composition comprises from about 5% to about 99% by weight of $CF_3CH=CHCl$ (HFCO-1233zd).

10. The method of claim 1 wherein the solvent composition comprises from about 5% to about 95% by weight of $CF_3CH=CHCl$ (HFCO-1233zd).

* * * * *